United States Patent [19]

Hahn

[11] 4,276,004

[45] Jun. 30, 1981

[54] INFUSION PUMP

[75] Inventor: Andreas Hahn, Hofolding, Fed. Rep. of Germany

[73] Assignee: Messerschmitt-Boelkow-Biochm Gesellschaft mit beschrankter Haftung, Munich, Fed. Rep. of Germany

[21] Appl. No.: 44,330

[22] Filed: May 31, 1979

[30] Foreign Application Priority Data

Jun. 14, 1978 [DE] Fed. Rep. of Germany ....... 2826033

[51] Int. Cl.$^3$ .................. F04B 43/14; A61M 5/00
[52] U.S. Cl. ................. 417/479; 128/214 F; 417/540
[58] Field of Search ........... 417/413, 566, 479; 128/214 F

[56] References Cited

U.S. PATENT DOCUMENTS

| 2,847,149 | 8/1958 | Ainsworth | 417/435 |
| 2,981,197 | 4/1961 | Dolza | 417/566 |
| 3,145,659 | 8/1964 | Suendsen | 417/479 |
| 4,121,584 | 10/1978 | Turner | 128/214 E |
| 4,140,118 | 2/1979 | Jassawalla | 128/214 F |
| 4,142,523 | 3/1979 | Stegeman | 128/214 R |
| 4,177,808 | 12/1979 | Malbec | 128/214 R |

FOREIGN PATENT DOCUMENTS

| 887429 | 8/1953 | Fed. Rep. of Germany | 417/479 |
| 2639992 | 9/1976 | Fed. Rep. of Germany | . |
| 2710269 | 3/1977 | Fed. Rep. of Germany | . |
| 2723197 | 5/1977 | Fed. Rep. of Germany | . |
| 2315578 | 12/1976 | France | 417/413 |

Primary Examiner—William L. Freeh
Attorney, Agent, or Firm—W. G. Fasse; D. F. Gould

[57] ABSTRACT

The present infusion pump has a housing with an insert in the housing which is closed by a cover. The insert has a bore defining the pump volume. The insert also defines passageways and at least one chamber in the pump. One of two membranes is held between the insert and the pump housing and forms an inlet valve. The other membrane is arranged between the insert and the cover and forms the pump membrane proper as well as an outlet valve. Normally, in the rest condition of the pump, a magnetic drive member urges a pressure element against the pump membrane and against the inlet valve membrane contrary to the force of a spring. In operation, the spring opens the inlet valve thereby also actuating the pump membrane for its suction stroke. The magnetic drive member returns the pump membrane and the inlet valve back into the rest position thereby actuating the pump membrane for its pressure stroke while closing the inlet valve.

5 Claims, 4 Drawing Figures

U.S. Patent    Jun. 30, 1981    4,276,004
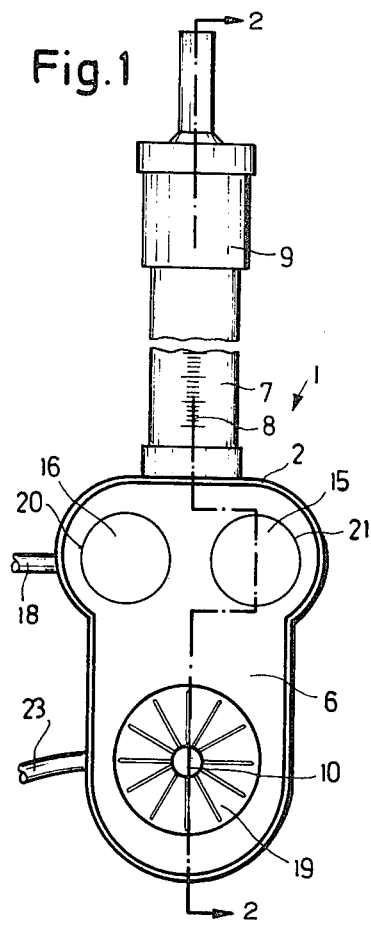
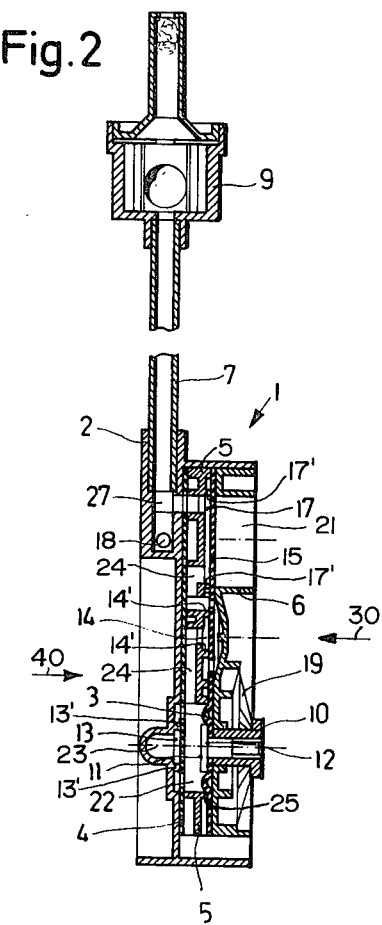
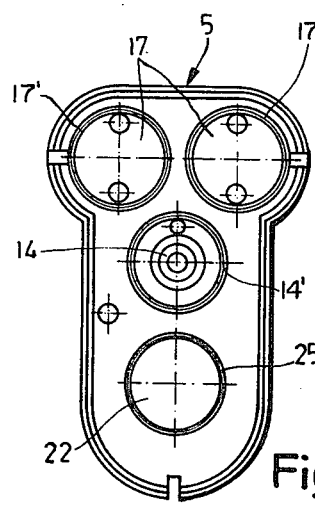
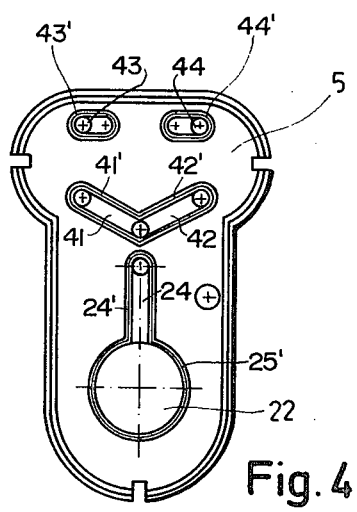

INFUSION PUMP

BACKGROUND OF THE INVENTION

The present invention relates to an infusion pump especially for human medical purposes.

Recent developments have replaced more and more the simple infusion devices by systems including pumps. Simple infusion devices used to place a container holding the infusion liquid at a level higher than the patient to use gravity as the necessary force causing the liquid flow. The more recent developments employ a pump for producing the necessary pressure for moving the infusion liquid. Systems employing a pump have the advantage, as compared to gravity fed devices, that the pump permits the use of the system even under limited space conditions, for example, when the patient is still in an ambulance thereby avoiding loss of time. In addition, pump operated systems have the advantage of being more precisely controllable and the infusion process can be more closely monitored. Suitable, pump operated devices are, for example, disclosed in German Patent Pulbication No. 1,911,919 and in German Pat. No. 2,209,322.

However, due to the increased technical sophistication of pump operated infusion devices, certain problems have arisen with regard to sterilizing the system including peripheral components and keeping the system germ-free as compared to gravity fed infusion devices. It has been found that the costs and the time necessary for a completely satisfactory sterilization is quite substantial where the pump and other components coming into contact with the infusion liquid are to be used repeatedly.

Furthermore, prior art infusion devices employing pumps, frequently comprise functional elements which are separated from each other including pumps, hose clamps, valves, pressure gauges and the like. The assembly and operation of these components may be rather cumbersome, which also applies to their sterilization.

OBJECTS OF THE INVENTION

In view of the above it is the aim of the invention to achieve the following objects singly or in combination:

to construct a compact infusion pump which forms with its cooperating components a functional, integral unit whereby the components are simple and few in number;

to construct the pump in such a manner that the pump will comprise all the components which form part of the so-called sterile zone;

to construct the infusion pump so that the formation of gas bubbles is substantially prevented;

to construct the infusion pump so that merely two membranes will be required at least one of which performs several functions, for example, the pumping function, a valve function, and an access or sensing; and to minimize the number of parts while still providing an efficiently operating infusion system.

SUMMARY OF THE INVENTION

According to the invention there is provided an infusion pump with an elastic, mechanically driven pump membrane which is characterized in that a membrane inlet valve of the pump is arranged opposite the pump membrane proper. The valve membrane of the pump inlet valve is held mechanically in the valve closing position by means of a force which is also effective on the pump membrane. The outlet valve is also a membrane valve having a further membrane which forms preferably part of the pump membrane. The outlet valve membrane cooperates with at least one chamber in such a manner that the pressure present in the chamber may be ascertained externally through a portion of the outlet valve membrane. The pump further comprises a riser pipe to which is connected the infusion conduit for the patient. More specifically, the infusion conduit is connected to the outlet port of the pump.

Advantages of the pump just defined are seen in that with a small number of simple, easily constructed structural components a compact device has been achieved which may be removed with two manual movements from a sterile packing for connection to a drive apparatus which does not form part of the invention. Such drive apparatus may, for example, be a magnetic drive operating the pump in a known manner. The time required for removing the pump from a sterile packing and connecting it to the drive is very small. Moreover, during operation of the present pump the monitoring of the infusion process is substantially facilitated due to the compact structure and the clear coordination of all functional components. Further, the occurrence of unpermissible pressures in the infusion conduit is automatically monitored by control means which senses the elastic membrane. Furthermore, the costs of pumps constructed as taught herein are substantially lower than comparable prior art pumps including the peripheral equipment. Therefore, it is not necessary to reuse the present pump structure thereby avoiding the costs and time consumption which was necessary heretofore for the sterilization of prior art pumping systems for infusion use.

BRIEF FIGURE DESCRIPTION

In order that the invention may be clearly understood, it will now be described, by way of example, with reference to the accompanying drawings, wherein:

FIG. 1 is an elevational view of the pump according to the invention of that side of the pump which faces the pump drive mechanism not shown;

FIG. 2 is a sectional view along section line 2—2 in FIG. 1;

FIG. 3 is a front view of an insert member used in the present pump; and

FIG. 4 is a rear view of the insert shown in FIG. 3.

DETAILED DESCRIPTION OF PREFERRED EXAMPLE EMBODIMENTS AND OF THE BEST MODE OF THE INVENTION:

FIGS. 1 and 2 show the infusion pump 1 according to the invention having a housing 2 which may preferably be made of transparent synthetic material. An insert or plate member 5 is held in position in the housing 2 by a cover 6. The insert or plate 5 is located between two elastic membranes 3 and 4 and the cover 6 clamps the entire structure together by conventional means to close the pump housing whereby the connection between the cover and the pump housing may be of a permanent kind, for example, by means of adhesive or welding. The membrane 3 forms a pump membrane and preferably also an outlet valve membrane. The membrane 4 forms an inlet valve membrane. A riser pipe 7 is operatively secured to the housing 2. The riser pipe 7 is also made of transparent synthetic material and is provided with a scale 8 for reading the level of liquid within the riser pipe. The topend of the riser pipe 7 is closed by an antiseptic cover member 9 of any desired, conventional construction.

The pump membrane 3 is held in place between the insert 5 and the cover 6. The inlet valve membrane 4 forming an inlet valve 13 is clamped in position between the housing 2 and the insert 5. The pump membrane 3 may be driven by magnetic drive means not shown but conventionally connectable to a force application member 10 for moving the member 10 against the force of a spring 19. In one position (not shown), the force application member 10 is located to the left away from the opposite position shown in FIG. 2. In the left position of member 10 the surface 11 of the member 10 touches the membrane 4 thereby holding the latter in an inlet valve closing position against the seat of the inlet valve 13. In this condition the drive mechanism operates against the force of the spring 19 which tends to bias the member 10 into the right position shown in FIG. 2.

Instead of using the member 10 it is also possible to use an armature exerting a pull in the manner just described. In this embodiment the force of the spring would be effective in the opposite direction. The membranes 3 and 4 as well as the inlet valve 13 would thus be continuously subject to the biasing force of the spring during non-use of the infusion pump. Accordingly these components would have to be dimensioned with due regard to such biasing force.

As seen in FIG. 2 the left end of the member 10 has a stop shoulder 12 which limits the movement of the member 10 to the right because the shoulder 12 rests through the pump membrane 3 against the fixed housing cover 6. As shown, the member 10 is in its right hand limit position.

The cover 6 of the pump 1 comprises bores 20 and 21 through which pressure sensors, not shown, may directly touch portions 15 and 16 of the pump membrane 3. Such pressure sensors may be used for controlling a monitoring device or the magnetic drive mechanism. The pressure sensors may also be utilized for providing an alarm signal. The membrane portions 15 and 16 preferably form integral parts of the pump membrane 3 and cover chambers 17 formed in the insert 5. The chambers 17 are operatively connected to the riser pipe 7 and to an outlet port 18 which constitutes the infusion conduit connected to a patient. Thus, by using pressure sensors of conventional construction with different threshhold or response values and with different operational or switching functions, the control function may correspond to the pressure in the riser pipe 7 or in the infusion pipe 18 which constitutes the outlet port and is connected to the patient. The pump membrane 3 further forms the seal on the valve seat 14' of the outlet valve 14 located between the pump volume 22 defined by the insert 5 and the chambers 17.

The membrane 4 rests against the valve seats 13' of the inlet valve 13 which is in fluid communication with the inlet conduit or port 23.

FIG. 3 shows a front view of the insert 5 as viewed in the direction of the arrow 30 in FIG. 2.

FIG. 4 is a rear view of the insert 5 as viewed in the direction of the arrow 40 in FIG. 2. A bore 22 extending entirely through the insert 5 defines the pump volume. The front fact of the insert 5 is provided with a seat 25 for the pump membrane 3. The back seat 25' shown in FIG. 4 rests against the inlet valve membrane 4. The pump volume 22 is connectable through the inlet valve 13 and through the inlet port 23 to a container holding infusion liquid not shown. Above the pump volume bore 22 there is centrally arranged the outlet valve 14 surrounded by the respective sealing seat 14'. The membrane 3 rests against the sealing seat. Above the outlet valve 14 there are arranged the chambers 17 also surrounded by respective sealing seats 17'. A channel 24 on the backside of insert 5 connects the pump volume 22 with the outlet valve 14. Channels 41 and 42 connect the outlet valve 14 with the chambers 17. Channels 43 and 44 connect the chambers 17 to the inlet 27 of the riser pipe 7 which is also connected to the outlet port 18. The channels 41 and 42 are surrounded by sealing seats 41' and 42'. Similarly, the channels 43 and 44 are surrounded by sealing seats 43' and 44'. The channel 24 is surrounded by a sealing seat 24'. Thus, sealing seats are provided on both sides of the insert 5.

The just described sealing seats in the insert 5 make sure that upon assembly of the membranes 3 and 4 and the insert 5 in the valve housing 2 a proper seal is accomplished around all hollow spaces inside the pump, especially the pump space 22, the outlet valve 14, the chamber 17, and the channel 24. Since the insert is located between the membranes 3 and 4, the membranes are capable of the just mentioned sealing function relative to the valve housing or the valve cover 6. This simple structure enables, for example, the membrane 3 to perform several functions, namely, to act as the pump membrane proper, as a valve membrane for the outlet valve 14 and also as pressure sensor membranes relative to the chambers 17. The insert 5 is of relatively simple constuction and may be made, for example, by injection molding, whereby well known thermoplastic materials may be used. Since the entire pump comprises essentially only six components namely, two membranes 3 and 4, the housing 2, the insert 5, the cover 6, and the riser pipe 7, a very competitive manufacturing cost has been achieved while simultaneously assuring with certainty the desired function.

The inlet 27 of the riser pipe 7 is located at a level higher than the outlet port 18. Thus, a trap for any gas bubbles is provided whereby the occurrence of gas bubbles in the conduit leading to the patient is prevented because gas bubbles would tend to travel through the riser pipe 7 where they may be discharged through the cap 9. This feature of the invention is further enhanced by the arrangement of the inlet valve.

When the pump according to the invention is to be used it is removed from a sterile packing not shown and connected with its member 10 to a drive mechanism, for example, a stroke or lifting magnetic drive. The pressure member 10 presses its lower surface 11 against the inlet valve membrane 4 of the inlet valve 13. Thereafter, the pressure sensors are inserted into cavaties 20 and 21 into contact with the membrane portions 15 and 16 of the membrane 3. Then the inlet port 23 is connected to a container holding infusion liquid and the outlet port 18 is connected to the patient whereupon the drive mechanism may be switched on. In operation, the level of liquid readable on the scale 8 in the riser pipe 7 will fluctuate up and down thereby providing an indication of the function of the infusion system as well as of the blood pressure in a vein of the patient.

If the maximum permissible pressure is exceeded, the pressure sensors in the cavaties 20 and 21 provide a respective control signal to the drive mechanism and simultaneously an alarm if desired. The just described infusion pump is very compact especially since it combines all components necessary for the operation and monitoring of the system in one single unit in the pump zone proper. This compact structure has the further advantage that relative short conduits are required for the infusion liquid making it possible to use the present system even where little space is available, for example, in an ambulance. The system further provides an increased safety for the patients because monitoring the system has been greatly simplified as no components are located outside a zone which may be readily observed by the operator. Further, the number of components that need monitoring has been minimized.

In the light of the above disclosure it will be appreciated that the two membranes which perform a plurality of functions are of the most simple construction, namely, plain and sheet-like and provided with the respective apertures cut into the elastic material of the membranes. The shape of the insert 5 is similarly simple yet, the insert 5 holds all the required recesses for the valves and the pump volume chambers and connecting channels. Only the inlet and outlet ports as well as the connection for the riser pipe 7 are provided in the valve housing proper.

By placing the inlet 27 of the riser pipe 7 slightly above the outlet port 18 a gas bubble trap is accomplished as described above and by making the riser pipe transparent, the continuous monitoring of the infusion liquid level is visually possible.

Moreover, it is virtually impossible to improperly handle the pump or damage it due to its full contained structure. The surface 11 and the shoulder 12 of the pressure member 10 provides the necessary stroke limitation and the fixed biasing of the pressure member 10 by the spring 19 also eliminates any action by the operator for any stroke adjustments.

Although the invention has been described with reference to specific example embodiments, it will be appreciated, that it is intended, to cover all modifications and equivalents within the scope of the appended claims.

What is claimed is:

1. An infusion pump, comprising pump housing means, inlet port means (23) and outlet port means (18) operatively connected to said pump housing means (2), pump membrane means (3) operatively supported in said pump housing means, inlet valve means (13) including inlet valve membrane means (4) operatively supported in said pump housing means substantially opposite said pump membrane means (3), whereby the pump membrane means cooperates in its one position with the inlet valve membrane means for closing the inlet valve means, drive means arranged for operatively applying, in one position of said drive means, a force to said pump membrane means (3) and simultaneously to said inlet valve membrane means (4) for holding the inlet valve means closed and for opening said inlet valve means while substantially simultaneously imparting a suction stroke to said pump membrane means when said drive means move into the opposite position, outlet valve means (14) including outlet valve membrane means operatively supported in said valve housing means, chamber means (17) positioned in said valve housing means, said outlet valve membrane means (14) comprising at least one membrane portion (15, 16) which is operatively arranged for closing said chamber means (17), access means (20, 21) in said pump housing means providing access to said at least one portion (15, 16) of said outlet valve membrane means (14) for ascertaining the pressure in said chamber means (17) by contacting said outlet valve membrane means (14), riser pipe means (7) operatively connected to said chamber means (17) and to said outlet port means (18), said infusion pump further comprising insert means (5) fitting into said pump housing means, and cover means forming part of said pump housing means for holding said insert means in said pump housing means, said insert means comprising a bore defining the pump volume, said insert means further comprising recess means forming part of said outlet valve means and said chamber means (17) which cooperate with said portion (15, 16) of said outlet valve membrane means, said insert means further forming connecting channel means between said inlet and outlet valve means and said chamber means.

2. The pump of claim 1, wherein said pump membrane means (3) and said outlet valve membrane means including said accessible membrane portion (15,16) comprise a single diaphragm.

3. The pump of claim 1, wherein said force applying drive means comprise a force application member (10) and spring means (19) arranged for cooperation with said force application member for applying said force to said pump membrane means, said force application member having seat means for limiting the stroke of said force application member and thus the movement of said pump membrane means (3).

4. The pump of claim 1, wherein said riser pipe means comprise an inlet end (27) located at a level higher than said outlet port means (18) for forming a bubble trap.

5. The pump of claim 4, wherein said riser pipe means are made of transparent material and has a rectangular cross-section, said riser pipe means further comprising scale means thereon for reading the level of liquid in said riser pipe means.

* * * * *

UNITED STATES PATENT OFFICE
CERTIFICATE OF CORRECTION

Patent No. 4,276,004　　　　　　　　　　Dated June 30, 1981

Inventor(s) Andreas Hahn

It is certified that error appears in the above-identified patent and that said Letters Patent are hereby corrected as shown below:

--[73] Assignee: Messerschmitt-Boelkow-Blohm Gesellschaft mit beschraenkter Haftung, Munich, Fed. Rep. of Germany--.

Signed and Sealed this

Twenty-second Day of September 1981

[SEAL]

Attest:

Attesting Officer

GERALD J. MOSSINGHOFF

Commissioner of Patents and Trademarks